US00PP13024P2

(12) United States Plant Patent
Danziger

(10) Patent No.: US PP13,024 P2
(45) Date of Patent: Oct. 1, 2002

(54) TORENIA PLANT NAMED 'DANTOGOLD'

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/503,359

(22) Filed: Feb. 14, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—Foley & Lardner

(57) ABSTRACT

A new and distinct Torenia plant named 'Dantogold' characterized by having an intense flower that is 3 cm in diameter with a dark-purple throat; vigorous, compact, semi-trailing growth habit; dark-green foliage; plant spread reaching almost 25–30 inches; and performs best as a pot plant in partial shade.

1 Drawing Sheet

BACKGROUND OF THE INVENTION

The present invention comprises a new and distinct cultivar of Torenia, known by the cultivar name 'Dantogold'. The cultivar 'Dantogold' was selected as a whole plant mutation of Torenia 'Suzie Wong' (unpatented) at Moshav Mishmar Hashiva, Israel, by the inventor Gabriel Danziger in June 1999.

The first act of asexual reproduction of 'Dantogold', was accomplished when vegetative cuttings were taken from the initial selection in August 1999 in a controlled environment in Mishmar Hashiva, Israel by a technician working under formulations established and supervised by the inventor. Horticultural examination of selected units initiated during 1999 has demonstrated that the combination of characteristics as herein disclosed for 'Dantogold' are firmly fixed and are retained through successive generations of asexual reproduction.

'Dantogold' has not been observed under all possible environmental conditions. The phenotype may vary somewhat with variations in environment such as temperature, light intensity and daylength, however, without any variations in genotype. The following observations, measurements and comparisons describe the plants grown in Mishmar Hashiva, Israel under greenhouse conditions which approximate those generally used in commercial practice.

BRIEF DESCRIPTION OF THE INVENTION

The following traits have been repeatedly observed and are determined to be basic characteristics of 'Dantogold' which in combination distinguish this Torenia as a new and distinct cultivar:

1. Intense yellow flower that is 3 cm in diameter with a dark-purple throat;
2. Vigorous, compact, semi-trailing growth habit;
3. Dark-green foliage;
4. Plant spread reaching almost 25–30 inches; and
5. Performs best as a pot plant in partial shade.

Of the many commercial cultivars known to the present inventor, the most similar in comparison to 'Dantogold' is Torenia 'Suzie Wong'. In comparison to Torenia 'Suzie Wong', 'Dantogold' has larger flowers, foliage which greener and larger, more vigorous growth, and better pot performance.

BRIEF DESCRIPTION OF THE DRAWING

The accompanying photographic illustration shows typical flower and foliage characteristics of 'Dantogold', with the color being as true as possible with illustrations of this type.

DETAILED BOTANICAL DESCRIPTION

In the following description color references are made to The Royal Horticultural Society (R.H.S.) Colour Chart. The color values were determined between 10:00 a.m. and 12:00 p.m. in October 1999 under full sunlight at Mishmar Hashiva, Israel. The plants decribed are 8 weeks old from planting.

Classification:
- *Botanical.*—A mutation of a hybrid of *Scrophulariaceae Torenia baillonii.*
- *Commercial.*—Torenia cultivar 'Dantogold'.

Plant:
- *Growth habit.*—Semi-prostrate.
- *Height.*—4 inches.
- *Spreading area.*—25–30 inches.
- *Blooming period.*—Almost all year round. Self-cleaning.

Stem:
- *Thickness.*—2–3 mm.
- *Color.*—Yellow-green, RHS 144A.
- *Pubescence.*—Few.
- *Branching.*—30–40 side shoots, 2 months after planting in summer.
- *Length of internode.*—6–7 cm.

Leaf:
- *Arrangement on stem.*—Opposite.
- *Shape.*—Oval.
- *Size.*—Length is 4 cm and width is 3.5 cm.
- *Thickness.*—Less than 1 mm.
- *Immature leaf color.*—Upper surface RHS 137C, lower surface RHS 146C.

*Mature leaf color.*—Upper surface RHS 137A, lower surface RHS 146B.

*Markings.*—Serrated acute.

*Pubescence.*—Few.

*Petiole.*—1.2–1.4 cm in length, color RHS 146A.

Flower:

*Lastingness of the individual bloom.*—2–3 days.

*Orientation at opening.*—Horizontal.

*Type.*—Single.

*Shape.*—Tubular.

*Diameter.*—30 mm.

*Bud.*—2.1 cm long, 0.7 cm wide; color yellow-green RHS 146A, emerging petals yellow-orange RHS 14A.

*Flower tube.*—Length 1.5 cm, color of outside of tube RHS 79A.

*Color.*—Petals are yellow-orange, RHS 17C, and yellow-orange RHS 14A on the back side; tubes are purple RHS 79A.

*Calyx.*—Tubular, 5 winged, separated at the top, length 15 mm, diameter 8 mm.

*Pedicel* (*length and color*).—2–3 cm, yellow-green, RHS 144A.

*Fragrance.*—None.

Reproductive organs:

*Pistil* (*number, color*).—One (1), purple, RHS 79A.

*Stamens* (*number*).—Four (4).

*Anther* (*color*).—Purple, RHS 79A.

*Filament* (*color*).—Purple, RHS 79A.

*Fruit/seeds.*—Seed capsule 0.5 mm in width, 1.5 mm in length.

Resistance: Susceptible to powdery mildew.

I claim:

1. A new and distinct Torenia plant named 'Dantogold', substantially as illustrated and described herein.

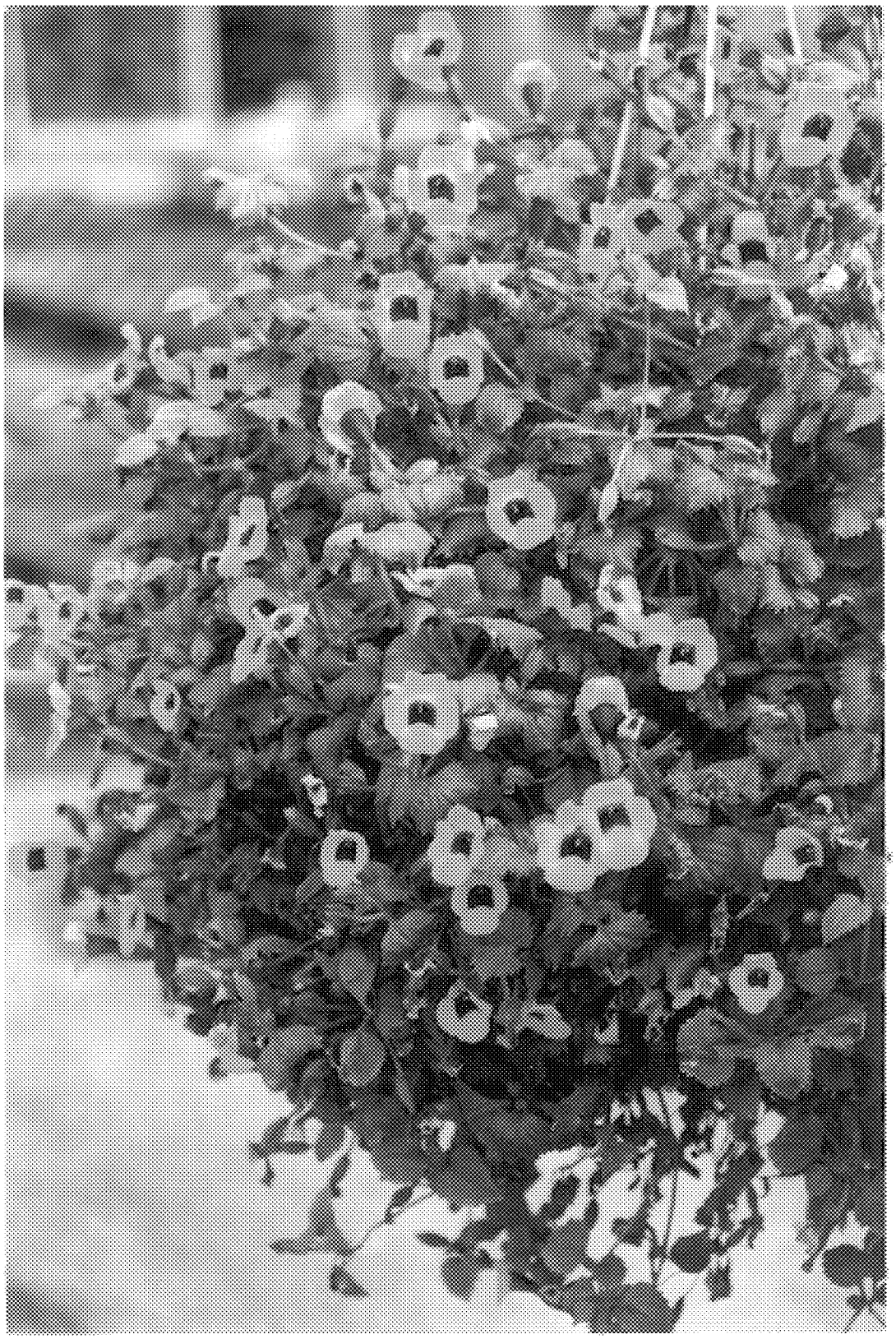

* * * * *